United States Patent [19]

Sugimoto et al.

[11] Patent Number: 4,921,863
[45] Date of Patent: May 1, 1990

[54] CYCLIC AMINE DERIVATIVES

[75] Inventors: Hachiro Sugimoto, Ushiku; Takaharu Nakamura, Abiko; Norio Karibe, Yatabe; Isao Saito, Sakura; Kunizou Higurashi, Tokyo; Masahiro Yonaga, Tsuchiura; Takeru Kaneko, Yatabe; Takahiro Nakazawa, Fujishiro; Masataka Ueno, Yatabe; Kiyomi Yamatsu, Kamakura, all of Japan

[73] Assignee: Eisai Co., Ltd., Tokyo, Japan

[21] Appl. No.: 177,662

[22] PCT Filed: Sep. 30, 1986

[86] PCT No.: PCT/JP86/00502
§ 371 Date: Feb. 17, 1988
§ 102(e) Date: Feb. 17, 1988

[87] PCT Pub. No.: WO88/02365
PCT Pub. Date: Apr. 7, 1988

[51] Int. Cl.$^5$ .................. A61K 31/445; C07D 211/00
[52] U.S. Cl. .................................... 514/319; 514/318; 540/575; 540/596; 540/597; 540/600; 540/609; 544/283; 544/335; 544/363; 544/391; 544/403; 546/146; 546/168; 546/174; 546/176; 546/194; 546/196; 546/197; 546/205; 546/206; 546/213; 546/225; 546/236; 546/237; 546/278; 546/281; 548/524; 548/539

[58] Field of Search .................. 546/205, 194, 206; 514/318, 319

[56] References Cited

U.S. PATENT DOCUMENTS 3,576,810  6/1968  Duncan et al. ............. 546/205
4,246,268  1/1981  Carr ........................... 546/205
4,665,076  5/1987  Mestre et al. ............... 546/205

Primary Examiner—Richard L. Raymond
Assistant Examiner—James H. Turnipseed
Attorney, Agent, or Firm—Birch, Stewart, Kolasch & Birch

[57] ABSTRACT

Cyclic amine derivatives of the formula:

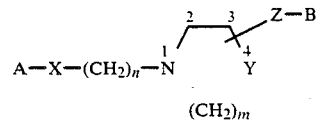

or the pharmacologically acceptable salts thereof, wherein the symbols are as defined in the specification, as effective in relieving, curing or preventing mental symptoms due to cerebral vascular disorders.

32 Claims, No Drawings

CYCLIC AMINE DERIVATIVES

FIELD OF INDUSTRIAL UTILIZATION

The present invention relates to cyclic amine derivatives having excellent medicinal activities.

Prior Art:

Various medicines for cerebral vascular disorders have been proposed. For example, cerebral vasodilator drugs and cerebral metabolism activators have been used. However, no drug which is drastically effective has been proposed as yet. At present, there is no drug effective particularly for cerebral vascular dementia and intellectual function disorders among the symptoms due to cerebral vascular disorders.

OBJECT OF THE INVENTION

After intensive investigations made for the purpose of finding a new compound effective for the treatment of various symptoms due to cerebral vascular disorders, particularly mental symptoms, over a long time under the above-mentioned circumstances, the inventors have found quite effective compounds. The present invention has been completed on the basis of this finding.

Therefore, an object of the present invention is to provide cyclic amine derivatives and pharmacologically acceptable salts thereof which are effective for the treatment of cerebral vascular disorders such as cerebral stroke, apoplexy, infarction and arteriosclerosis and mental symptoms due to multiple infarct dementia. Another object of the invention is to provide a process for producing said compounds or pharmacologically acceptable salts thereof. Still another object of the invention is to provide medicines containing said compound or a pharmacologically acceptable salt thereof as the active ingredient.

Construction and Effect of the Invention:

The intended compounds of the present invention are cyclic amine derivatives of the general formula (I) or pharmacologically acceptable salts thereof:

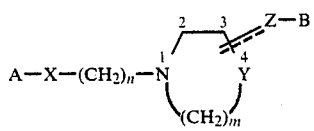

wherein A represents a substituted or unsubstituted phenyl, pyridyl or thienyl group, substituted or unsubstituted naphthyl, tetralyl, quinolyl, benzofuranyl, quinazolyl or benzothienyl group or a group of the formula:

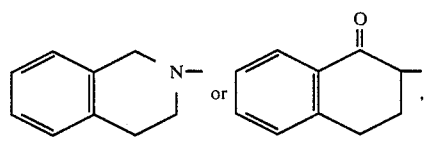

X represents a group of the formula:

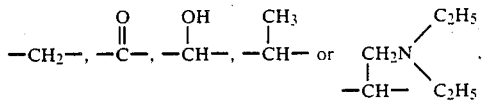

n represents an integer of 0 to 4,
m represents an integer of 1 to 3,
Y represents a carbon or nitrogen atom,
Z represents a group of the formula: —CH$_2$—,

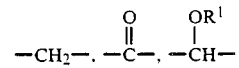

in which R$^1$ is a hydrogen atom or a lower alkyl, acyl, arylalkyl or heteroarylalkyl group,

in which Hal is a halogen atom,

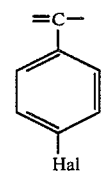

in which Hal is a halogen atom,

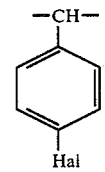

in which Hal is a halogen atom or

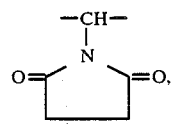

the symbol "=====" between Y and Z represents a single or double bond, the group of the formula: "===== Z–B" is bonded with the ring in the above formula at the 3- or 4-position, and B represents a phenyl or naphthyl group which may be substituted with one or two substituents which may be the same or different and which are selected from the group consisting of halogens, lower alkyl groups and lower alkoxy groups.

The lower alkyl groups in the above-mentioned definitions of R$^1$ and B include, for example, straight-chain or branched alkyl groups having 1 to 6 carbon atoms such as methyl, ethyl, n-propyl, n-butyl, isopropyl, isobutyl, 1-methylpropyl, tertbutyl, n-pentyl, 1-ethylpropyl, isoamyl and n-hexyl groups. Among them, methyl and ethyl groups are the most preferred.

The lower alkoxy groups in the above-mentioned definition of B are those derived from the abovementioned lower alkyl groups. Preferred examples of them include methoxy, ethoxy, propoxy, isopropoxy, butoxy and isobutoxy groups.

The substituents of the "substituted or unsubstituted phenyl group "0 and "substituted or unsubstituted naphthyl group" in the definition of A include, for example, the above-defined lower alkyl and alkoxy groups, hydroxyl group, halogen atoms such as fluorine, bromine, iodine and chlorine, phenyl group and heterocyclic groups having nitrogen atom(s) as the hetero atom such as imidazolyl, pyridyl and pyrazolyl groups. Said compounds may have one to three of these substituents. When the compounds have two or more of these substituents, they may be the same or different.

The phenyl group may have a methylenedioxy or ethylenedioxy group bonded with two different carbon atoms constituting the phenyl ring in addition to the above-mentioned substituents. Further, the substituted phenyl group includes also a group of the formula:

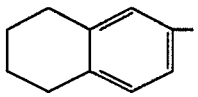

The acyl groups in the definition of $R^1$ include organic acid residues such as saturated aliphatic, unsaturated aliphatic, carbocyclic and heterocyclic carboxylic acid residues. Examples of them include lower alkanoyl groups such as formyl, acetyl, propionyl, butyryl, isobutyryl, valeryl, isovaleryl and pivaloyl groups, aroyl groups such as benzoyl, toluoyl and naphthoyl groups and heteroaroyl groups such as furoyl, nicotinoyl and isonicotinoyl groups.

The arylalkyl groups in the definition of $R^1$ include, for example, those derived from substituted or unsubstituted phenyl and naphthyl groups. Typical examples of them include benzyl and phenethyl groups. The substituents in the above definition include, for example, the above-defined lower alkyl and lower alkoxy groups, hydroxyl group and halogen atoms such as fluorine, bromine, iodine and chlorine atoms.

Typical examples of the heteroarylalkyl groups include pyridylalkyl groups such as the picolyl group.

The halogen atoms include fluorine, chlorine, bromine and iodine atoms.

The pharmacologically acceptable salts are ordinary non-toxic salts, for example, inorganic acid salts such as hydrochlorides, hydrobromides, sulfates and phosphates; organic acid salts such as acetates, maleates, tartrates, methanesulfonates, benzenesulfonates and toluenesulfonates; and amino acid salts such as arginine salts, aspartates and glutamates.

Production Processes

The compounds of the present invention can be produced by various processes. A typical example of these processes comprises:

$$A-X+CH_2)_{n-1}CH_2-Hal \quad (II)$$

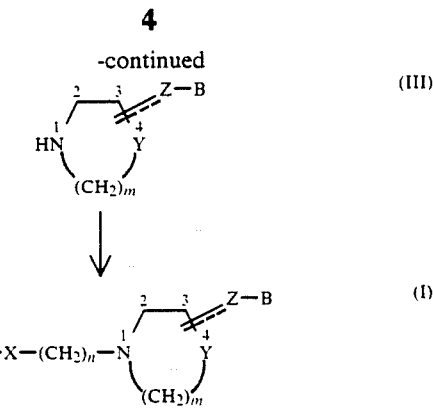

wherein Hal represents a halogen atom and A, X, Y, Z, B, n, m and  Z-B are as defined above.

Namely, a halide of the general formula (II) is reacted with a compound of the general formula (III) to obtain an intended compound of the general formula (I).

The dehydrohalogenation reaction is carried out by heating in an ordinary manner without using any solvent or in an organic solvent inert to the reaction which is selected from the group consisting of alcoholic solvents such as methanol, ethanol and butanol, benzene, toluene, xylene, tetrahydrofuran, chloroform, carbon tetrachloride and dimethylformamide. Preferred results are obtained when the reaction is carried out in the presence of an inorganic salt such as sodium hydrogencarbonate, potassium carbonate, sodium carbonate or sodium hydroxide or an organic base such as triethylamine, pyridine, pyrimidine or diethylaniline.

It is apparent from the pharmacological experiments described below that the compounds of the present invention have excellent pharmacological effects on the central nervous system, particularly a remarkable reparative effect on ischemic cerebral vascular disorders. Therefore, these compounds are useful for relieving, remedying or preventing mental disorders due to the cerebral vascular disorders such as cerebral stroke, apoplexy, infarction, arteriosclerosis and dementias, e.g. multiple infarct dementia.

It has been found in toxicity tests effected by using rats that the compounds of the present invention have a high safety and, therefore, the invention is highly valuable also in this regard.

According to the toxicity tests of typical compounds of the present invention (see Examples 1 to 12 given below), $LD_{50}$ of them was 2,000 to 4,000 mg/kg (oral administration to rats).

The compounds of the present invention used as the medicine are given either orally or parenterally. The dose of said compounds is not particularly limited, since it varies depending on the symptoms; age, sex, body weight and sensitivity of the patient; period and intervals of the administration; properties, composition and kind of the medicinal preparation; and varieties of active ingredients. Usually, about 0.1 to 300 mg/day, preferably about 1 to 100 mg/day of the compound is administered 1 to 4 times a day.

The compounds of the present invention are used in the form of a medicinal preparation such as an injection, suppository, sublingual tablet, tablet or capsule.

In the preparation of the injection, a pH adjustor, buffer, suspending agent, solubilizer, stabilizer, isotonizer, preservative, etc. are added to the active ingredient to form an intravenous, subcutaneous or intramuscular injection by an ordinary method. If necessary, the injection can be freeze-dried by an ordinary method.

Examples of the suspending agents include methylcellulose, Polysorbate 80, hydroxyethylcellulose, acacia, tragacanth gum powder, sodium carboxymethylcellulose and polyoxyethylenesorbitan monolaurate.

Examples of the solubilizers include polyoxyethylene hardened castor oil, Polysorbate 80, nicotinamide, polyoxyethylene sorbitan monolaurate, macrogol and ethyl esters of castor oil fatty acids.

Examples of the stabilizers include sodium sulfite, sodium metasulfite and ether. Examples of the preservatives include methyl hydroxybenzoate, ethyl hydroxybenzoate, sorbic acid, phenol, cresol and chlorocresol.

EXAMPLES

Typical examples of the compounds of the present invention will be shown below for facilitating the understanding of the present invention, which by no means limit the scope of the invention.

EXAMPLE 1

2-{2-[4-(p-Fluorobenzyl)piperidinyl]ethyl}naphthalene hydrochloride:

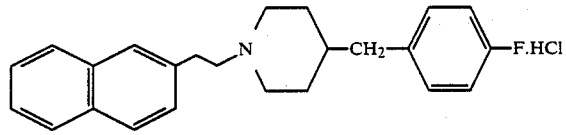

1.05 g of 1-chloro-2-(2-naphthyl)ethane, 1.09 g of 4-(p-fluorobenzyl)piperidine, 0.2 g of potassium iodide and 1.4 g of sodium hydrogencarbonate were refluxed in n-butanol solvent for 5 h. Then, the solvent was filtered out and 100 ml of chloroform was added to the residue. The mixture was washed with water and dried over magnesium sulfate. The oily product thus obtained was purified according to silica gel column chromatography and converted into its hydrochloride by an ordinary method.

Yield: 0.45 g
Melting point: 244° C.
Elementary analysis for $C_{24}H_{26}NF \cdot HCl$:

|  | C | H | N |
|---|---|---|---|
| calculated (%) | 75.08 | 7.09 | 3.65 |
| found (%) | 75.30 | 7.32 | 7.34 |

EXAMPLE 2

2-(4-Benzylpiperidinyl)-2'-acetonaphthone hydrochloride:

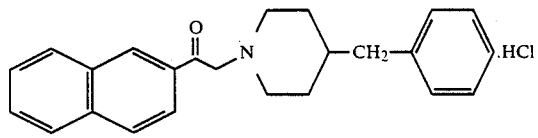

5 g of 2-bromo-2'-acetonaphthone, 3.5 g of 4-benzylpiperidine, 0.2 g of potassium iodine and 5 g of sodium hydrogencarbonate were refluxed in butanol solvent for 4 h. After completion of the reaction, the product was treated by an ordinary process. The oily product thus obtained was purified according to silica gel column chromatography and converted into its hydrochloride, which was then recrystallized from chloroform and ethanol.

Yield: 2.1 g
Melting point: 233° to 235° C.
Elementary analysis for $C_{24}H_{25}NO \cdot HCl$:

|  | C | H | N |
|---|---|---|---|
| calculated (%) | 75.87 | 6.90 | 3.69 |
| found (%) | 75.67 | 6.71 | 3.49 |

EXAMPLE 3

2-[4-Bis(4-fluorophenyl)methylene-1-piperidinyl]-2'-acetonaphthone hydrochloride:

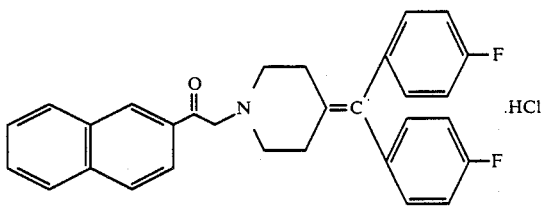

850 mg of 4-bis(4-fluorophenyl)methylenepiperidine, 700 mg of 2-bromo-2'-acetonaphthone, 20 mg of potassium iodide and 760 mg of sodium hydrogencarbonate were refluxed in n-butanol solvent for 3.5 h. After completion of the reaction, the product was treated by an ordinary process. The obtained oily product was purified according to silica gel column chromatography and converted into its hydrochloride to obtain 510 mg of the intended product.

Melting point: 214° to 217° C.
Elementary analysis for $C_{30}H_{25}NOF_2 \cdot HCl$

|  | C | H | N |
|---|---|---|---|
| calculated (%) | 73.54 | 5.35 | 2.86 |
| found (%) | 73.54 | 5.46 | 3.03 |

EXAMPLE 4

4-(1-Naphthonyl)piperidinyl-3',4'-dimethylacetophenone hydrochloride:

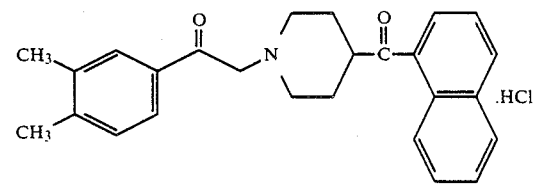

1.9 g of 2-bromo-3',4'-dimethylacetophenone, 2.0 g of 4-(1-naphthonyl) piperidine, 0.1 g of potassium iodide and 2.1 g of sodium hydrogencarbonate were refluxed in n-butanol solvent for 3 h. After completion of the reaction, the product was treated by an ordinary process. The obtained oily product was purified according to silica gel column chromatography and converted into its hydrochloride to obtain 1.0 g of the intended product.

Melting point: 92° to 96° C. (dec.)

Elementary analysis for $C_{26}H_{27}NO_2 \cdot HCl$:

| | C | H | N |
|---|---|---|---|
| calculated (%) | 74.01 | 6.68 | 3.32 |
| found (%) | 73.79 | 6.69 | 3.01 |

EXAMPLE 5

1-[3-(p-Fluorobenzoyl)piperidinyl]-2'-acetonaphthone hydrochloride:

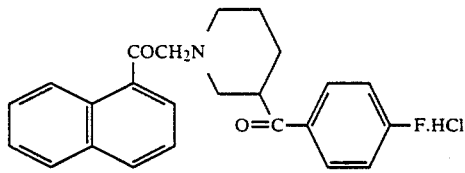

0.7 g of 1-bromo-2'-acetonaphthone, 0.7 g of 3-(p-fluorobenzoyl)piperidine hydrochloride, 0.05 g of potassium iodide and 0.7 g of sodium hydrogencarbonate were refluxed in n-butanol solvent for 2 h. After completion of the reaction, the product was treated by an ordinary process. The obtained oily product was purified according to silica gel column chromatography and converted into its hydrochloride.

Yield: 0.4 g
Melting point: 123° to 127° C. (dec.)
Elementary analysis for $C_{24}H_{22}NO_2F \cdot HCl$:

| | C | H | N |
|---|---|---|---|
| calculated (%) | 69.98 | 5.63 | 3.40 |
| found (%) | 69.76 | 5.51 | 3.18 |

EXAMPLE 6

2-[4-(α-Benzyloxy-p-fluorobenzyl)piperidinyl]-2'-acetonaphthone hydrochloride:

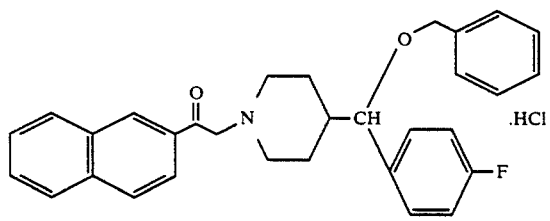

1.1 g of 2-bromo-2'-acetonaphthone, 1.2 g of 4-(α-benzyloxy-p-fluorobenzyl)piperidine and 4.5 g of sodium hydrogencarbonate were refluxed in ethanol solvent for 3.5 h. After completion of the reaction, the product was treated by an ordinary process. The oily product thus obtained was purified according to silica gel column chromatography and converted into its hydrochloride, which was recrystallized from ethyl acetate/methanol.

Yield: 0.6 g
Melting point: 115° to 120° C.
Elementary analysis for $C_{31}H_{30}NO_2F \cdot HCl$:

| | C | H | N |
|---|---|---|---|
| calculated (%) | 76.76 | 6.44 | 2.89 |

| | C | H | N |
|---|---|---|---|
| found (%) | 76.59 | 6.21 | 2.68 |

EXAMPLE 7

2-[4-(α-Acetoxy-p-fluorobenzyl)piperidinyl]-2'-acetonaphthone hydrochloride

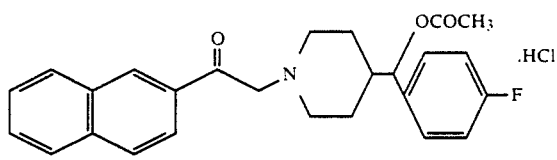

5.4 g of 2-bromo-2'-acetonaphthone, 4.6 of 4-(α-hydroxy-p-fluorobenzyl)piperidine and 10 g of sodium hydrogencarbonate were refluxed in ethanol solvent for 2.5 h. After completion of the reaction, the product was treated by an ordinary process. The obtained oily product was purified according to silica gel column chromatography to obtain 5 g of 2-[4-(α-hydroxy-p-fluorobenzyl)piperidinyl]-2'-acetonaphthone; 1 g of this product was stirred together with 1.0 g of acetic anhydride and 0.1 g of dimethylaminopyridine in pyridine solvent at room temperature for 5 h. After completion of the reaction, the oily product was purified according to silica gel column chromatography and converted into its hydrochloride, which was recrystallized from ethyl acetate and methanol.

Yield: 1.0 g
Melting point: 148° to 152° C.
Elementary analysis for $C_{26}H_{26}NO_3F \cdot HCl$:

| | C | H | N |
|---|---|---|---|
| calculated (%) | 68.49 | 5.97 | 3.07 |
| found (%) | 68.24 | 5.88 | 3.12 |

EXAMPLE 8

4-(4-p-Fluorobenzoyl)piperidinyl-6,7-dimethoxyisoquinoline hydrochloride

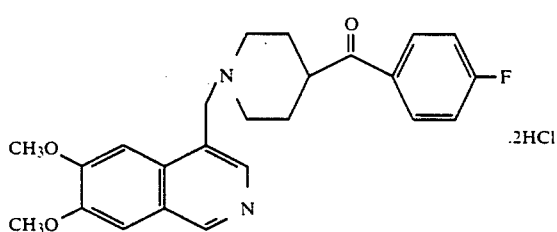

70 mg of 4-chloromethyl-6,7-dimethoxyisoquinoline was dissolved in 10 ml of dimethyl sulfoxide. 1 ml of triethylamine and 140 mg of 4-(p-fluorobenzoyl) piperidine were added to the solution and the mixture was heated to 80° C. for 1 h. The reaction mixture was dissolved in ethyl acetate, washed with water and dried over magnesium sulfate. The product was purified according to silica gel column chromatography and converted into its hydrochloride.

Yield: 80 mg
Melting point: 185° to 190° C.

Elementary analysis for $C_{24}H_{25}N_2O_3F \cdot 2HCl$:

|  | C | H | N |
|---|---|---|---|
| calculated (%) | 59.88 | 5.65 | 5.82 |
| found (%) | 59.78 | 5.61 | 5.80 |

EXAMPLE 9

4-{2-[4-(p-Fluorobenzoyl)piperidinyl]ethyl}quinazoline hydrochloride

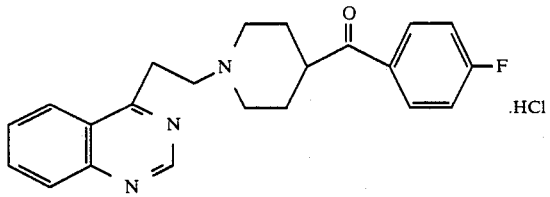

2 g of 4-methylquinazoline was dissolved in 20 ml of ethanol. 3.4 g of 4-(p-fluorobenzoyl)piperidine hydrochloride and 1.9 ml of 37% formalin were added to the solution and the mixture was stirred at room temperature for three days. A white precipitate was recovered by filtration and washed with ethanol to obtain the intended product.

Yield: 4.4 g
Melting point: 135° to 140° C.
Elementary analysis for $C_{22}H_{22}N_3OF \cdot HCl$:

|  | C | H | N |
|---|---|---|---|
| calculated (%) | 66.08 | 5.79 | 10.51 |
| found (%) | 66.02 | 5.65 | 10.44 |

EXAMPLE 10

1-(2-Naphthyl)-1-[4-(p-fluorobenzoyl)piperidinyl]-2-diethylaminoethane hydrochloride:

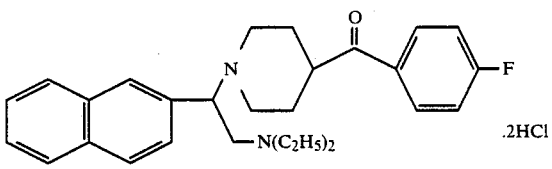

1.4 g of 1-(2-naphthyl)-2-diethylaminoethanol was dissolved in 20 ml of dichloromethane. 2.4 ml of triethylamine and 0.9 ml of methanesulfonyl chloride were added to the solution under cooling with ice and the mixture was stirred at room temperature for 4.5 h. A solution of 1.2 g of 4-(p-fluorobenzoyl)piperidine in 25 ml of dioxane was added to the reaction mixture and the obtained mixture was refluxed for 2 h. After completion of the reaction, the product was purified according to silica gel column chromatography and then converted into its hydrochloride.

Yield: 1.9 g
Melting point: 140° to 145° C.
Elementary analysis for $C_{28}H_{33}N_2OF \cdot 2HCl$:

|  | C | H | N |
|---|---|---|---|
| calculated (%) | 66.52 | 6.97 | 5.54 |
| found (%) | 66.57 | 6.81 | 5.38 |

EXAMPLE 11

2-[4-(α-Succinimido-p-fluorobenzyl)piperidinyl]-2'-accetonaphthone hydrochloride

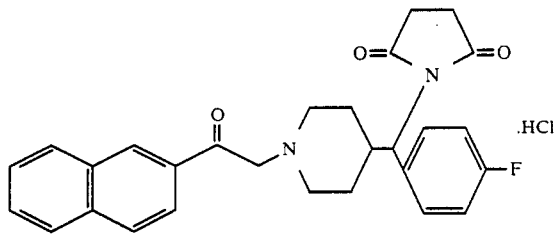

470 mg of 4-(α-succinimido-p-fluorobenzyl)piperidine was dissolved in 40 ml of ethanol. 410 mg of 2-bromo-2'-acetonaphthone and 420 mg of sodium hydrogencarbonate were added to the solution and the mixture was refluxed for 30 min. After completion of the reaction, the product was treated by an ordinary process. The obtained product was purified according to silica gel column chromatography and converted into its hydrochloride.

Yield: 400 mg
Melting point: 233° to 237° C.
Elementary analysis for $C_{28}H_{27}N_2O_3F \cdot HCl$:

|  | C | H | N |
|---|---|---|---|
| calculated (%) | 67.94 | 5.70 | 5.66 |
| found (%) | 68.13 | 5.56 | 5.47 |

EXAMPLE 12

2-[4-(p-Fluorobenzoyl)-1-piperidinyl]-2'-acetonaphthone hydrochloride

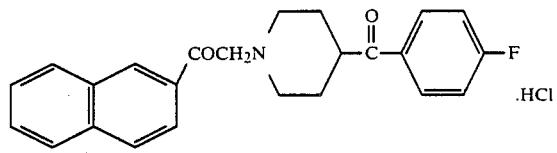

49.7 g of 2-bromo-2'-acetonaphthone, 49.9 g of 4-(p-fluorobenzoyl)piperidine hydrochloride, 0.5 g of potassium iodide and 50.4 g of sodium hydrogencarbonate were added to 500 ml of ethanol and the mixture was refluxed for 2 h. The solvent was distilled off and chloroform was added to the residue. The mixture was washed with water and dried. Chloroform was distilled off and the residue was purified according to silica gel column chromatography to obtain 58.9 g of the crystalline intended product, which was converted into its hydrochloride and recrystallized by an ordinary process to obtain the intended hydrochloride.

Melting point: 247° to 248° C. (dec.)
Elementary analysis for $C_{24}H_{22}NO_2F \cdot HCl$:

|  | C | H | N |
|---|---|---|---|
| calculated (%) | 69.98 | 5.63 | 3.40 |
| found (%) | 69.81 | 5.51 | 3.36 |

EXAMPLES 13 to 95

Compounds shown in Table 1 were prepared in the same manner as in Examples 1 to 12.

TABLE 1

| Example No. | Structural formula | Melting point (°C.) | Chemical formula | Elementary analysis (%) calculated/found | | |
|---|---|---|---|---|---|---|
| | | | | C | H | N |
| 13 | 4-F-C6H4-CO-piperidine-N-CH2CH2-CONH-C6H4-4-F · HCl | 234~235 (dec.) | $C_{21}H_{23}N_2O_2F_2 \cdot HCl$ | 61.68 / 61.49 | 5.92 / 5.85 | 6.85 / 6.77 |
| 14 | 4-F-C6H4-CO-piperidine-N-CH2-CH(OH)-C6H5 · HCl | 216~218 (dec.) | $C_{20}H_{22}NO_2F \cdot HCl$ | 66.02 / 66.16 | 6.37 / 6.39 | 3.85 / 3.77 |
| 15 | 4-F-C6H4-CO-piperidine-N-CH2-CO-C6H4-4-F · HCl | 228~229 (dec.) | $C_{20}H_{19}NO_2F_2 \cdot HCl$ | 63.24 / 63.11 | 5.31 / 5.37 | 3.69 / 3.58 |
| 16 | 4-F-C6H4-CO-piperidine-N-CH2CH2-C6H4-4-F · HCl | 223~224 (dec.) | $C_{20}H_{21}NOF_2 \cdot HCl$ | 65.66 / 65.39 | 6.06 / 6.12 | 3.83 / 3.81 |
| 17 | 4-F-C6H4-CO-piperidine-N-CH2CH2-C6H4-4-OCH3 · HCl | 225~226 (dec.) | $C_{21}H_{24}NO_2F \cdot HCl$ | 70.28 / 69.97 | 7.02 / 7.13 | 3.90 / 3.88 |
| 18 | 4-CH3-C6H4-CH2-piperidine-N-CH2CH2-C6H4-4-OCH3 · HCl | 201~202 | $C_{21}H_{27}NO \cdot HCl$ | 72.92 / 72.76 | 8.16 / 8.23 | 4.05 / 4.11 |
| 19 | 4-F-C6H4-CO-piperidine-N-CH2-CO-C6H5 · HCl | 233~235 (dec.) | $C_{20}H_{20}NO_2F \cdot HCl$ | 66.38 / 66.27 | 5.85 / 5.82 | 3.87 / 3.85 |

TABLE 1-continued

| Example No. | Structural formula | Melting point (°C.) | Chemical formula | Elementary analysis (%) calculated/found | | |
|---|---|---|---|---|---|---|
| | | | | C | H | N |
| 20 | 4-F-C6H4-CO-piperidine-N-CH2-CO-C6H3(3,4-diCH3)·HCl | 244~245 | $C_{22}H_{24}NO_2F \cdot HCl$ | 67.77 67.80 | 6.46 6.47 | 3.59 3.57 |
| 21 | C6H5-CH2-piperidine-N-CH2-CO-C6H5·HCl | 211~211.5 | $C_{20}H_{23}NO \cdot HCl$ | 72.82 72.19 | 7.33 7.13 | 4.25 4.12 |
| 22 | 4-F-C6H4-CO-piperidine-N-CH2-CO-C6H3(3,4-diCl)·HCl | 222~223 (dec.) | $C_{20}H_{18}NO_2FCl_2 \cdot 2HCl$ | 55.75 55.71 | 4.44 4.50 | 3.25 3.26 |
| 23 | (4-F-C6H4)2C=piperidine-N-CH2-CO-C6H5·HCl | 235~236 | $C_{26}H_{23}NOF_2 \cdot HCl$ | 70.98 70.59 | 5.50 5.63 | 3.18 3.34 |
| 24 | (4-F-C6H4)2CH-piperidine-N-CH2-CO-C6H5·HCl | 143~146 | $C_{26}H_{25}NOF_2 \cdot HCl$ | 70.66 70.43 | 5.93 5.91 | 3.17 3.24 |

TABLE 1-continued

| Example No. | Structural formula | Melting point (°C.) | Chemical formula | Elementary analysis (%) calculated/found C | H | N |
|---|---|---|---|---|---|---|
| 25 | (3,4-dimethylphenyl-CO-CH₂-N-piperidine-3-CO-C₆H₄-F)·HCl | 65~69 | $C_{22}H_{24}NO_4F·HCl$ | 62.63 / 62.48 | 5.97 / 5.70 | 3.39 / 3.11 |
| 26 | (3,4-dimethoxyphenyl-CO-CH₂-N-piperidine-4-CO-C₆H₄-F)·HCl | 234~236 (dec.) | $C_{22}H_{24}NO_4F·HCl$ | 62.63 / 62.57 | 5.97 / 5.96 | 3.32 / 3.15 |
| 27 | (pyridin-4-yl-CH₂CH₂-N-piperidine-4-CO-C₆H₄-F)·2HCl | 223~226 (dec.) | $C_{19}H_{21}N_2OF·2HCl$ | 59.23 / 59.18 | 6.02 / 6.11 | 7.27 / 7.02 |
| 28 | (pyridin-4-yl-CH₂-N-piperidine-4-CH(OH)-C₆H₄-F)·2HCl | 155~160 (dec.) | $C_{18}H_{21}N_2OF·2HCl$ | 57.91 / 57.80 | 6.21 / 6.12 | 7.50 / 7.20 |
| 29 | (pyridin-4-yl-CH₂-N-piperidine-4-CO-C₆H₄-F)·2HCl | 220~225 (dec.) | $C_{18}H_{19}N_2OF·2HCl$ | 58.23 / 58.25 | 5.70 / 5.71 | 7.55 / 7.43 |
| 30 | (pyridin-4-yl-CH₂-N-piperidine-4-CO-naphthyl)·2HCl | 121~125 (dec.) | $C_{22}H_{22}N_2O·HCl$ | 63.01 / 62.91 | 5.77 / 5.73 | 6.68 / 6.59 |

TABLE 1-continued

| Example No. | Structural formula | Melting point (°C.) | Chemical formula | Elementary analysis (%) calculated/found | | |
|---|---|---|---|---|---|---|
| | | | | C | H | N |
| 31 | 4-biphenyl-O-(CH$_2$)$_3$-N(piperidine)-C(=O)-C$_6$H$_4$-F · HCl | 238~240 | C$_{27}$H$_{20}$NO$_2$F·HCl | 71.42 / 71.13 | 6.44 / 6.29 | 3.09 / 3.10 |
| 32 | pyridin-3-yl-C(=O)-CH$_2$-N(piperidine)-CH$_2$-C$_6$H$_5$ · HCl | 173~174 | C$_{19}$H$_{22}$N$_2$O·HCl | 68.98 / 68.75 | 7.01 / 6.89 | 8.47 / 8.26 |
| 33 | thiophen-2-yl-C(=O)-CH$_2$-N(piperidine)-C(=O)-C$_6$H$_4$-F · HCl | 243~244 | C$_{18}$H$_{18}$NO$_2$F·HCl | 58.77 / 58.61 | 5.21 / 5.51 | 3.81 / 3.91 |
| 34 | 4-biphenyl-C(=O)-CH$_2$-N(piperidine)-C(=O)-C$_6$H$_4$-F · HCl | 253~254 (dec.) | C$_{26}$H$_{24}$NO$_2$F·HCl | 71.31 / 71.51 | 5.75 / 6.03 | 3.20 / 3.25 |
| 35 | pyridin-4-yl-C$_6$H$_4$-C(=O)-CH$_2$-N(piperidine)-C(=O)-C$_6$H$_4$-F · 2HCl | 269~270 (dec.) | C$_{23}$H$_{23}$N$_3$O$_2$F·2HCl | 59.36 / 59.23 | 5.41 / 5.40 | 9.03 / 9.11 |
| 36 | naphth-2-yl-NH-C(=O)-(CH$_2$)$_2$-N(piperidine)-C(=O)-C$_6$H$_4$-F · HCl | 182~184 | C$_{25}$H$_{25}$N$_2$O$_2$F·HCl | 68.10 / 68.31 | 5.94 / 5.96 | 6.35 / 6.22 |
| 37 | naphth-2-yl-C(=O)-CH$_2$-N(piperidine)-C(=O)-C$_6$H$_4$-OCH$_3$ · HCl | 232~234 (dec.) | C$_{25}$H$_{25}$NO$_3$·HCl | 70.83 / 70.76 | 6.18 / 6.09 | 3.30 / 3.21 |

TABLE 1-continued

| Example No. | Structural formula | Melting point (°C.) | Chemical formula | Elementary analysis (%) calculated/found | | |
|---|---|---|---|---|---|---|
| | | | | C | H | N |
| 38 | naphthalene-CH2-C(=O)-CH2-N(piperidine)-C(=O)-C6H4-Cl·HCl | 242~244 (dec.) | $C_{24}H_{22}NO_2Cl·HCl$ | 67.30 / 67.22 | 5.41 / 5.35 | 3.27 / 3.31 |
| 39 | naphthalene-CH2CH2-N(piperidine)-C(=O)-C6H4-F·HCl | 253~255 (dec.) | $C_{24}H_{24}NOF·HCl$ | 72.44 / 72.40 | 6.33 / 6.38 | 3.52 / 3.49 |
| 40 | tetrahydroisoquinoline-CH2CH2-N(piperidine)-C(=O)-C6H4-F·2HCl | 199~200 (dec.) | $C_{24}H_{29}N_2OF·2HCl$ | 63.57 / 63.47 | 6.89 / 6.78 | 6.18 / 6.26 |
| 41 | 3,4-dimethoxybenzyl-N(CH2CH2)-N(piperidine, 4-OH)-CH-C6H4-F·2HCl | 198~200 (dec.) | $C_{24}H_{35}N_2O_3F·2HCl$ | 60.58 / 60.43 | 7.24 / 7.12 | 5.44 / 5.63 |
| 42 | naphthalene-C(=O)-O-CH2CH2-N(piperidine)-C(=O)-C6H4-F·HCl | 209~210 (dec.) | $C_{25}H_{24}NO_3F·HCl$ | 67.94 / 68.01 | 5.70 / 5.81 | 3.17 / 3.01 |
| 43 | naphthalene-S-CH2CH2CH2-N(piperidine)-C(=O)-C6H4-F·HCl | 195~196 (dec.) | $C_{25}H_{24}NOSF·HCl$ | 67.62 / 67.82 | 6.13 / 6.17 | 3.15 / 2.89 |

TABLE 1-continued

| Example No. | Structural formula | Melting point (°C.) | Chemical formula | Elementary analysis (%) calculated/found | | |
|---|---|---|---|---|---|---|
| | | | | C | H | N |
| 44 | benzodioxane-C(O)-CH2-N(piperidine)-C(O)-C6H4F·HCl | 253~254 (dec.) | C22H21NO4F·HCl | 63.08 63.16 | 5.29 5.36 | 3.14 3.32 |
| 45 | tetralone-CH2-N(piperidine)-C(O)-C6H4F·HCl | 180~181 | C23H24NO2F·HCl | 68.73 68.88 | 6.27 6.32 | 3.49 3.39 |
| 46 | naphthalene-C(O)-CH2-CH2-N(piperidine)-C(O)-C6H4F·HCl | 209~210 (dec.) | C25H24NO2F·HCl | 70.49 70.40 | 5.92 5.85 | 3.29 3.35 |
| 47 | (CH3O)2-C6H3-CH2-N-CH2-CH2-N(piperidine)-CH2-C6H5·2HCl | 266~267 (dec.) | C25H34N2O2·2HCl | 64.23 64.36 | 7.76 7.72 | 5.99 6.11 |
| 48 | quinoline-CH2-CH2-CH2-N(piperidine)-C(O)-C6H4F·2HCl | 214~217 (dec.) | C22H23N2OF·2HCl | 62.71 62.77 | 5.50 5.43 | 6.65 6.72 |
| 49 | naphthalene-C(O)-CH2-N(piperazine)-CH2-C6H5·2HCl | 260~263 (dec.) | C23H23N2OF·2HCl | 63.45 63.16 | 5.79 5.81 | 6.43 6.36 |

TABLE 1-continued
| Example No. | Structural formula | Melting point (°C.) | Chemical formula | Elementary analysis (%) calculated/found | | |
|---|---|---|---|---|---|---|
| | | | | C | H | N |
| 50 | 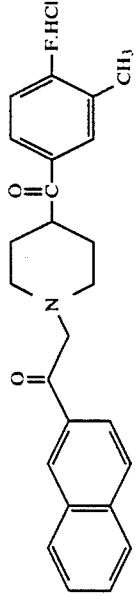 | 236–237 (dec.) | $C_{25}H_{24}NO_2F \cdot HCl$ | 70.50 70.31 | 5.92 5.86 | 3.29 3.31 |
| 51 | 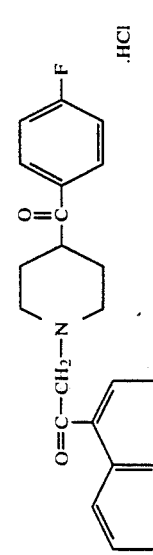 | 242 (dec.) | $C_{25}H_{24}NO_2F \cdot HCl$ | 70.50 70.37 | 5.92 5.96 | 3.29 3.31 |
| 52 | 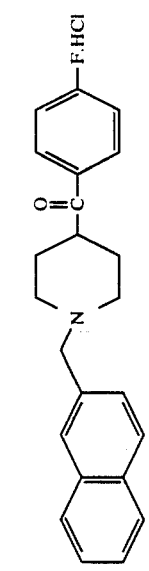 | 237–238 (dec.) | $C_{23}H_{22}NOF \cdot HCl$ | 71.96 71.88 | 6.04 6.12 | 3.65 3.57 |
| 53 | 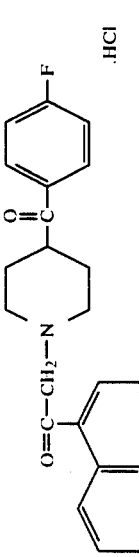 | 231–232 (dec.) | $C_{24}H_{23}NO_2Cl \cdot HCl$ | 69.57 69.48 | 6.08 6.16 | 3.38 3.42 |
| 54 | 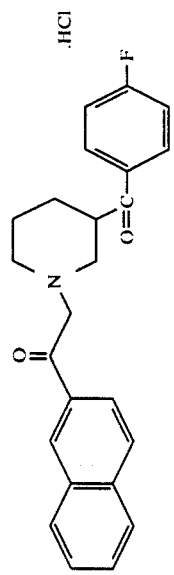 | 153–156 | $C_{24}H_{22}NO_2F \cdot HCl$ | 69.98 70.12 | 5.63 5.58 | 3.40 3.26 |

TABLE 1-continued

| Example No. | Structural formula | Melting point (°C.) | Chemical formula | Elementary analysis (%) calculated/found C | H | N |
|---|---|---|---|---|---|---|
| 55 | (1,4-dimethylnaphthalene-CO-CH2-N-piperidine-CH2-phenyl · HCl) | 222~225 (dec.) | C25H27NO·HCl | 76.22 75.93 | 7.16 7.33 | 3.56 3.47 |
| 56 | (naphthalene-2-CO-CH2-N-piperidine-CO-4-methylphenyl · HCl) | 250~253 (dec.) | C25H25NO2·HCl | 73.61 73.48 | 6.42 6.33 | 3.43 3.19 |
| 57 | (4-chloronaphthalene-1-CO-CH2-N-piperidine-CO-4-fluorophenyl · HCl) | 256~260 (dec.) | C24H21NO2ClF·HCl | 67.45 67.18 | 5.19 5.06 | 3.28 3.14 |
| 58 | (naphthalene-2-CH(OH)-CH2-N-piperidine-CO-4-fluorophenyl · HCl) | 246~248 (dec.) | C24H24NO2F·HCl | 69.64 69.61 | 6.08 6.02 | 3.38 3.14 |
| 59 | (naphthalene-2-CO-CH2CH2CH2-N-piperidine-CO-4-fluorophenyl · HCl) | 250~254 (dec.) | C24H24NO2F·HCl | 70.98 70.96 | 6.19 6.14 | 3.18 3.20 |

TABLE 1-continued

| Example No. | Structural formula | Melting point (°C.) | Chemical formula | Elementary analysis (%) calculated/found C | H | N |
|---|---|---|---|---|---|---|
| 60 | (4-F-phenyl-C(=O)-piperidine-N-COCH$_2$-O-naphthyl) · HCl | 223~226 (dec.) | C$_{24}$H$_{22}$NO$_2$F·HCl | 69.98 / 69.86 | 5.63 / 5.58 | 3.40 / 3.22 |
| 61 | (4-F-phenyl-CH$_2$-piperidine-N-CH$_2$-C(=O)-tetrahydronaphthyl) · HCl | 272~274 (dec.) | C$_{22}$H$_{27}$NOF·HCl | 62.87 / 62.69 | 6.65 / 6.54 | 6.38 / 6.28 |
| 62 | (4-F-phenyl-NCO-piperazine-N-CH$_2$-C(=O)-tetrahydronaphthyl) · HCl | 214~217 (dec.) | C$_{23}$H$_{25}$N$_3$O$_2$F·HCl | 66.26 / 66.13 | 6.29 / 6.25 | 6.72 / 6.47 |
| 63 | (4-F-phenyl-C(=O)-piperidine-N-CH$_2$-C(=O)-tetrahydronaphthyl) · HCl | 263~266 (dec.) | C$_{23}$H$_{26}$NO$_2$F·HCl | 68.39 / 68.18 | 6.74 / 6.55 | 3.47 / 3.41 |
| 64 | (4-F-phenyl-CH$_2$-piperazine-N-CH$_2$-quinoline) · 3HCl | 234~238 (dec.) | C$_{21}$H$_{22}$N$_3$F·3HCl | 56.71 / 56.45 | 5.66 / 5.58 | 9.45 / 9.17 |
| 65 | (4-F-phenyl-C(=O)-piperazine-N-CH$_2$-quinoline) · 2HCl | 230~233 (dec.) | C$_{21}$H$_{20}$N$_3$OF·2HCl | 59.73 / 59.54 | 5.25 / 5.13 | 9.94 / 9.78 |

TABLE 1-continued

| Example No. | Structural formula | Melting point (°C.) | Chemical formula | Elementary analysis (%) calculated/found | | |
|---|---|---|---|---|---|---|
| | | | | C | H | N |
| 66 | (structure with 4-fluorophenyl, OC$_2$H$_5$, piperidine, naphthalene ketone) ·HCl | 142~147 | C$_{24}$H$_{28}$NO$_2$F·HCl | 70.66<br>70.53 | 6.61<br>6.50 | 3.17<br>3.06 |
| 67 | (structure with pyridine, fluorophenyl, piperidine, naphthalene) ·2HCl | 98~104 | C$_{30}$H$_{29}$N$_2$O$_2$F·2HCl | 66.54<br>66.42 | 5.77<br>5.68 | 5.17<br>5.07 |
| 68 | (structure with 4-fluorophenyl, piperidine, benzodioxin) ·HCl | 135~140 | C$_{22}$H$_{22}$NO$_4$F·HCl | 62.93<br>62.69 | 5.52<br>5.41 | 3.34<br>3.17 |
| 69 | (structure with OH, 4-fluorophenyl, piperidine, naphthalene) | 162~164 | C$_{25}$H$_{24}$NO$_2$F | 76.37<br>76.03 | 6.41<br>6.40 | 3.71<br>3.56 |
| 70 | (structure with OH, 4-fluorophenyl, piperidine, N-CH(benzyl), naphthalene) ·HCl | 236~237 (dec.) | C$_{31}$H$_{30}$NO$_2$F·HCl | 73.86<br>73.92 | 6.20<br>6.21 | 2.78<br>2.78 |

TABLE 1-continued

| Example No. | Structural formula | Melting point (°C.) | Chemical formula | Elementary analysis (%) calculated/found C | H | N |
|---|---|---|---|---|---|---|
| 71 | naphthalene-C(=O)-CH2-N(piperidine)-C(=O)-C6H5 ·HCl | 242~245 | C24H25NO2·HCl | 73.18 / 73.33 | 6.14 / 6.18 | 3.56 / 3.66 |
| 72 | naphthalene-C(=O)-CH2-N(piperidine)-CH2OCH2-C6H5 ·HCl | 182~183 | C25H27NO2·HCl | 73.25 / 73.26 | 6.88 / 6.76 | 3.42 / 3.24 |
| 73 | naphthalene-CH2CH2-N(piperidine)-CH2-C6H5 ·HCl | 222~223 | C24H27N·HCl | 78.77 / 78.73 | 7.11 / 7.64 | 3.83 / 3.62 |
| 74 | naphthalene-C(=O)-CH2-N(piperidine)=CH-C6H4F ·HCl | 246~246.5 | C24H22NOF·HCl | 72.81 / 72.66 | 5.81 / 5.70 | 3.54 / 3.45 |
| 75 | naphthalene-C(=O)-CH2-N(piperidine)-CH2-C6H4F ·HCl | 243~244 | C24H24NOF·HCl | 72.44 / 72.39 | 6.33 / 6.47 | 3.52 / 3.50 |
| 76 | benzofuran-C(=O)-CH2-N(piperidine)-C(=O)-C6H4F ·HCl | 224~225 | C22H20NO3F·HCl | 65.75 / 65.79 | 5.27 / 5.26 | 3.49 / 3.36 |

TABLE 1-continued

| Example No. | Structural formula | Melting point (°C.) | Chemical formula | Elementary analysis (%) calculated/found | | |
|---|---|---|---|---|---|---|
| | | | | C | H | N |
| 77 | naphthalene-CO-CH2-N(piperazine)N-CO-C6H4-F · HCl | 206~207 | $C_{23}H_{21}N_2O_2F \cdot HCl$ | 66.90 / 66.82 | 5.37 / 5.36 | 6.78 / 6.80 |
| 78 | naphthalene-CH(OH)-CH2-N(piperidine)-CH(OH)-C6H4-F · HCl | 173~174 | $C_{24}H_{27}NO_2F \cdot HCl$ | 69.14 / 69.02 | 6.77 / 6.51 | 3.36 / 3.27 |
| 79 | naphthalene-CHCl-CH2-N(piperidine)-CO-C6H4-F · HCl | 187~188 | $C_{24}H_{23}NOFCl \cdot HCl$ | 66.67 / 66.43 | 5.59 / 5.33 | 3.24 / 3.12 |
| 80 | naphthalene-CH2-N(piperidine)-CH2-C6H5 · HCl | 172~173 | $C_{23}H_{25}N \cdot HCl$ | 78.50 / 78.64 | 7.45 / 7.37 | 3.98 / 3.84 |
| 81 | naphthalene-CH2-CH2-N(piperidine)-CH2-C6H5 · HCl | 226~227 | $C_{24}H_{27}N \cdot HCl$ | 78.76 / 78.75 | 7.45 / 7.40 | 3.83 / 3.78 |
| 82 | naphthalene-CH2-CH2-N(piperazine)N-CH2-C6H5 · 2HCl | 274~275 | $C_{23}H_{24}N_2 \cdot 2HCl$ | 68.48 / 68.52 | 7.00 / 7.02 | 6.94 / 6.87 |

TABLE 1-continued

| Example No. | Structural formula | Melting point (°C.) | Chemical formula | Elementary analysis (%) calculated/found | | |
|---|---|---|---|---|---|---|
| | | | | C | H | N |
| 83 | 4-F-C6H4-CH=piperidine-CH2CH2-naphthalene ·HCl | 249 | $C_{24}H_{24}NF \cdot HCl$ | 75.48 / 75.44 | 6.60 / 6.45 | 3.67 / 3.82 |
| 84 | 4-F-C6H4-CH(OH)-CH2-piperidine-CH2-naphthalene ·HCl | 203 | $C_{24}H_{24}NOF \cdot HCl$ | 72.44 / 72.11 | 6.33 / 6.19 | 3.52 / 3.59 |
| 85 | Ph-CH2-piperidine-CH2-CH(OH)-naphthalene ·HCl | 216~217 | $C_{24}H_{27}NO \cdot HCl$ | 75.47 / 75.48 | 7.39 / 7.40 | 3.67 / 3.64 |
| 86 | Ph-CH=piperidine-CH2-C(O)-naphthalene ·HCl | 239~241 | $C_{24}H_{25}NO \cdot HCl$ | 76.28 / 76.08 | 6.40 / 6.30 | 3.71 / 3.69 |
| 87 | Ph-CH2-piperidine-CH2-C(O)-benzofuran ·HCl | 221~223 | $C_{22}H_{23}NO_2 \cdot HCl$ | 71.44 / 71.16 | 6.54 / 6.58 | 3.79 / 4.03 |
| 88 | 4-F-C6H4-C(O)-piperidine-CH2CH2-C6H3(OH) ·HCl | 227~229 | $C_{28}H_{38}NO_2F \cdot HCl$ | 70.64 / 70.58 | 8.26 / 8.14 | 2.94 / 2.73 |

TABLE 1-continued
| Example No. | Structural formula | Melting point (°C.) | Chemical formula | Elementary analysis (%) calculated/found | | |
|---|---|---|---|---|---|---|
| | | | | C | H | N |
| 89 | 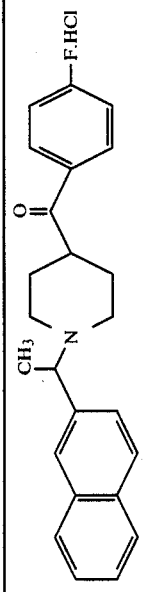 | 205~210 (dec.) | C₂₄H₂₄NOF·HCl | 72.44 72.41 | 6.33 6.19 | 3.52 3.41 |
| 90 | 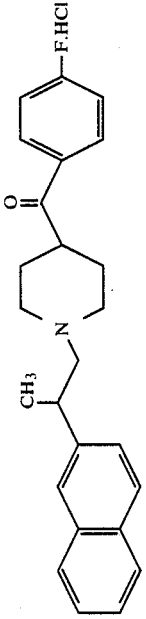 | 195~197 (dec.) | C₂₅H₂₆NOF·HCl | 72.89 72.83 | 6.60 6.54 | 3.40 3.37 |
| 91 | 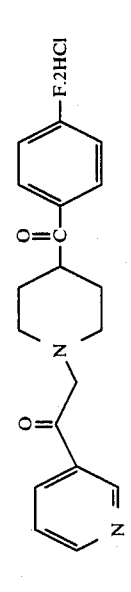 | oily | C₁₉H₁₉N₂O₂F·2HCl | 57.15 56.78 | 5.30 5.14 | 7.02 6.87 |
| 92 | 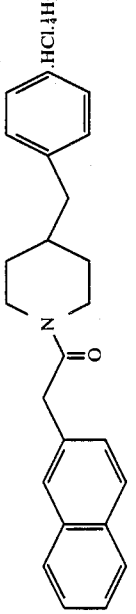 | 233.5~235 | C₂₄H₂₅NO·HCl·½H₂O | 74.98 74.90 | 6.95 6.92 | 3.64 3.69 |
| 93 | 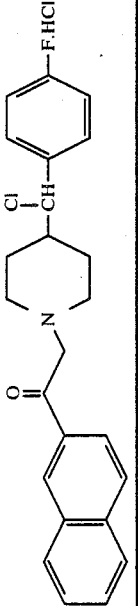 | oily | C₂₄H₂₃NOFCl·HCl | 66.67 66.39 | 5.59 5.62 | 3.24 3.24 |

The examples of pharmacological experiments of the compounds of the present invention will be given below:

EXPERIMENTAL EXAMPLE 1

Effect of Protecting Ischemic Brain

Carotid arteries of both sides of ICR mice 6 to 8 weeks old) were exposed under halothane anesthesia and ligated. The mice thus treated had stroke symptoms such as jumping, rolling and convulsion and almost all of them died within 24 h.

The compound of the present invention was administered orally to the mice one hour before the ligation and the survival time (maximum: 6 h) was examined as an index of the effect of protecting the ischemic brain. In this experiment, the compound was used in the form of a 5% suspension in acacia and a 5% acacia solution was given to the control group.

The results are shown in Table 2. It is apparent that the compounds of the present invention had a life-prolonging effect, while the average survival time of the control group was 149.9 min.

TABLE 2

Effect of protecting ischemic brain

| Compound used | Dose (mg/kg, p.o.) | Number of cases | Average survival time (min) (average ± S.E.) | % |
|---|---|---|---|---|
| Control group | — | 26 | 149.9 ± 25.8 | 100 |
| Compound of Example 12 | 3 | 10 | 213.7 ± 52.3 | 143 |
| | 10 | 10 | 181.4 ± 43.6 | 121 |
| | 30 | 9 | 191.1 ± 54.3 | 128 |
| Compound of Example 73 | 10 | 7 | 150.4 ± 57.6 | 100 |
| | 30 | 6 | 275.2 ± 58.2 | 184 |
| Compound of Example 74 | 3 | 10 | 143.3 ± 39.6 | 96 |
| | 10 | 7 | 205.1 ± 43.6 | 137 |
| | 30 | 7 | 194.2 ± 49.7 | 130 |

EXPERIMENTAL EXAMPLE 2

Effect of Remedying Learning Disorder After Ischemia

Common carotid arteries on both sides of Mongolian gerbils (17 to 21 weeks old) were clipped with Skoville clamps without anesthesia and the clamps were removed after 5 min to realize a short period of ischemia. Twenty-four hours after the removal of the clamps, these animals were subjected to learning and memory tests were conducted after an additional 24 h.

The learning and memory functions were examined by the passive avoidance method with a modification of a device reported by Jarvik and Kopp in "Psychological Reports", 21, 221 to 224 (1967). The device had two chambers, i.e. a well-lighted chamber A and a dark chamber B. In the tests, the animals were placed in the well-lighted chamber A and an electric current (A.C., 1.6 mA) was applied to a grid on the floor of the dark chamber B for 5 min when they entered the chamber B.

On the next day, the animals subjected to the learning were placed in the chamber A and the time (latent time) which had elapsed before they entered the chamber B was measured. The upper limit of the latent time was set at 300 sec.

The compound was administered in the form of a 5% suspension in acacia orally one hour before causing the ischemia. A 5% acacia solution was administered to the control group.

The results are shown in Table 3. The average latent time of the normal (pseudo-operation) group was 246.5 sec and that of the control group was as short as 71.5 sec. Namely, the learning and memory functions of them were damaged by the 5-min ischemia. When the compounds of the present invention were administered to the control group, the latent time was elongated again, namely the learning disorder after the ischemia was remedied.

TABLE 3

Effects of remedying learning disorder after ischemia

| Compound used | Dose (mg/kg. p.o.) | Number of cases | Latent time (sec) (average ± S.E.) | Recovery* ratio (%) |
|---|---|---|---|---|
| Normal group | — | 65 | 246.5 ± 10.9 | 100 |
| Control group | — | 62 | 71.5 ± 11.7 | 0 |
| Compound of Example 12 | 3 | 22 | 168.8 ± 23.0 | 56 |
| | 10 | 24 | 196.8 ± 22.3 | 72 |
| | 30 | 11 | 196.3 ± 37.0 | 71 |
| Compound of Example 73 | 10 | 8 | 193.1 ± 35.3 | 69 |
| | 30 | 7 | 80.1 ± 28.2 | 5 |
| Compound of Example 74 | 3 | 13 | 110.2 ± 29.0 | 22 |
| | 10 | 24 | 123.2 ± 24.3 | 30 |
| | 30 | 21 | 129.2 ± 23.8 | 33 |

*The recovery ratio was calculated according to the following formula for each latent time:
$$\frac{\text{(treated group)} - \text{(control group)}}{\text{(normal group)} - \text{(control group)}} \cdot 100$$

EXPERIMENTAL EXAMPLE 3

Effect of Protecting Cells From Disorder After Ischemia

Carotid arteries on both sides of Mongolian gerbils were blocked to realize cerebral ischemia for 5 min. As a result, the nerve cells in the CAI region of the hippocampus disappeared extensively [Karino, T.: Brain Res., 239, 57 to 69 (1982)].

The compound of the present invention was administered orally to them, while a 5% acacia suspension was administered to the control group. After one hour, the ischemia was realized for 5 min. After one week, the animal was perfused and fixed with 4% neutral formalin transcardially. The treated sample was embedded in paraffin and cut to obtain slices having a thickness of 3 $\mu$m. The slices were dyed with hematoxylin-eosin and the number of the nerve cells in the CAI region of the hippocampus of each slice was counted.

The results are shown in Table 4. The nerve cell density in the CAI region of the hippocampus was 287/mm in the normal (pseudo-operation) group and that of the control group was as small as 21/mm. Namely, a serious disappearance of the cell was caused by the 5-min ischemia. On the other hand, when the compound of the present invention was administered, the nerve cell density was increased to prove the effect thereof in protecting the cells from the disorder.

TABLE 4

Effect of protecting the cells from disorder after ischemia

| Compound used | Dose (mg/kg, p.o.) | Number of cases | Nerve cell density (number/mm) |
|---|---|---|---|
| Normal group | — | 6 | 287 ± 6 |
| Control group | — | 16 | 21 ± 10 |
| Compound of Example 12 | 3 | 8 | 62 ± 26 |
| | 10 | 10 | 75 ± 32 |
| | 30 | 10 | 83 ± 32 |
| Compound of Example 73 | 10 | 7 | 69 ± 21 |
| | 30 | 5 | 49 ± 8 |
| Compound of | 30 | 8 | 62 ± 5 |

TABLE 4-continued

| | Effect of protecting the cells from disorder after ischemia | |
|---|---|---|
| Compound used | Dose (mg/kg, p.o.) | Number of cases | Nerve cell density (number/mm) |
| Example 74 | | | |

We claim:

1. Cyclic amine derivatives of the following formula or pharmacologically acceptable salts thereof:

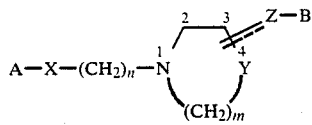

wherein A represents naphthyl optionally substituted by halogen, or lower alkyl; or the group

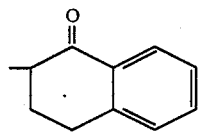

has been substituted therefor
X represents a group of the formula:

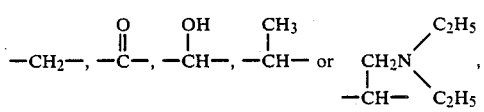

n represents an integer of 0 to 4, m represents 2 Y represents a carbon atom, Z represents a group of the formula: —CH$_2$—

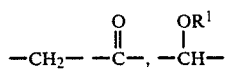

in which R$^1$ is a hydrogen atom or a lower alkyl, acyl, arylalkyl or heteroarylalkyl group

in which Hal is a halogen atom, =CH—,

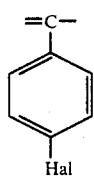

in which Hal is a halogen atom,

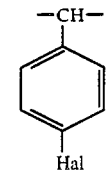

in which Hal is a halogen atom or

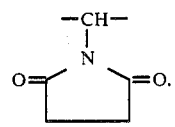

the symbol "═════" between Y and Z represents a single or double bond,
the group of the formula: "═════ Z–B" is bonded with the ring in the above formula at the 3- or 4-position, and
B represents a phenyl or naphthyl group which may be substituted with one or two substituents which may be the same or different and which are selected from the group consisting of halogens, lower alkyl groups and lower alkoxy groups.

2. Cyclic amine derivatives and pharmacologically acceptable salts thereof according to claim 1, wherein X is a group of the formula:

3. Cyclic amine derivatives and pharmacologically acceptable salts thereof according to claim 2, wherein B is a phenyl group which may be substituted with one or two substituents which may be the same or different and which are selected from the group consisting of halogens, lower alkyl groups and lower alkoxy groups.

4. Cyclic amine derivatives and pharmacologically acceptable salts thereof according to claim 3 wherein B is a phenyl group which is substituted with a halogen.

5. Cyclic amine derivatives and pharmacologically acceptable salts thereof according to claim 1, wherein X is a group of the formula:

and n is 1.

6. Cyclic amine derivatives and pharmacologically acceptable salts thereof according to claim 5, wherein Z is a group of the formula:

7. Cyclic amine derivatives and pharmacologically acceptable salts thereof according to claim 6, wherein B is a phenyl group which may be substituted with one or two halogen atoms.

8. Cyclic amine derivatives and pharmacologically acceptable salts thereof according to claim 1, wherein X is a group of the formula:

Z is a group of the formula:

—CH$_2$— and B is a phenyl group substituted with a halogen.

9. Cyclic amine derivatives and pharmacologically acceptable salts thereof according to claim 1, wherein X is a group of the formula: —CH$_2$—.

10. A cyclic amine derivative or a pharmacologically acceptable salt thereof according to claim 1, which is 2-{2-[4-(p-fluorobenzyl)piperidinyl]ethyl}naphthalene.

11. A cyclic amine derivative or a pharmacologically acceptable salt thereof according to claim 1, which is 2-(4-benzylpiperidinyl)-2'-acetonaphthone.

12. A cyclic amine derivative or a pharmacologically acceptable salt thereof according to claim 1, which is 2-[4-bis(4-fluorophenyl)methylene-1-piperidinyl]-2'-acetonaphthone.

13. A cyclic amine derivative or a pharmacologically acceptable salt thereof according to claim 1, which is 1-[3-(p-fluorobenzoyl)piperidinyl]-2'-acetonaphthone.

14. A cyclic amine derivative or a pharmacologically acceptable salt thereof according to claim 1, which is 2-[4-(α-benzyloxy-p-fluorobenzyl)piperidinyl]-2'-acetonaphthone.

15. A cyclic amine derivative or a pharmacologically acceptable salt thereof according to claim 1, which is 2-[4-(α-acetoxy-p-fluorobenzyl)piperidinyl]-2'-acetonaphthone.

16. A cyclic amine derivative or a pharmacologically acceptable salt thereof according to claim 1, which is 1-(2-naphthyl)-1-[4-(p-fluorobenzoyl)piperidinyl]-2-diethylaminoethane.

17. A cyclic amine derivative or a pharmacologically acceptable salt thereof according to claim 1, which is 2-[4-(α-succinimido-p-fluorobenzyl)piperidinyl]-2'-acetonaphthone.

18. Cyclic amine derivatives and pharmacologically acceptable salts thereof according to claim 1, wherein A is a naphthyl group, X is a group of the formula: —CH$_2$—, n is 1, m is 2, Y is a carbon atom and ═══════ Z-B is a benzyl group in the 4-position.

19. Cyclic amine derivatives and pharmacologically acceptable salts thereof according to claim 1, wherein A is a naphthyl group, X is a group of the formula:

n is 1, Y is a carbon atom and ═══════ Z-B is a group of the formula:

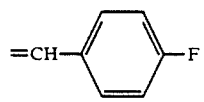

in the 4-position.

20. Cyclic amine derivatives and pharmacologically acceptable salts thereof according to claim 1, wherein X is a group of the formula: —CHOH—.

21. Cyclic amine derivatives and pharmacologically acceptable salts thereof according to claim 1, wherein X is a group of the formula: —CHOH— and n is 1.

22. Cyclic amine derivatives and pharmacologically acceptable salts thereof according to claim 1, wherein X is a group of the formula: —CHOH—, Z is a group of the formula: —CH$_2$— and B is a phenyl group substituted with halogen.

23. Cyclic amine derivatives and pharmacologically acceptable salts thereof according to claim 1, wherein A is a naphthyl group, and X is a group of the formula: —CHOH—.

24. Cyclic amine derivatives and pharmacologically acceptable salts thereof according to claim 1, wherein A is a naphthyl group, X is a group of the formula: —CHOH—, n is 1, m is 2, Y is a carbon atom and Z-B is a group of the formula:

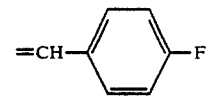

in the 4-position.

25. Cyclic amine derivatives and pharmacologically acceptable salts thereof according to claim 20, wherein B is a phenyl group which may be substituted with one or two substituents which may be the same or different and which are selected from the group consisting of halogen, lower alkyl groups and lower alkoxy groups.

26. Cyclic amine derivatives and pharmacologically acceptable salts thereof according to claim 25, wherein B is a phenyl group which is substituted with a halogen.

27. Cyclic amine derivatives and pharmacologically acceptable salts thereof according to claim 21, wherein Z is a group of the formula:

28. Cyclic amine derivatives and pharmacologically acceptable salts thereof according to claim 27, wherein B is a phenyl group which may be substituted with one or two halogen atoms.

29. A cyclic amine derivative or a pharmaceutically acceptable salt of a compound of the formula:

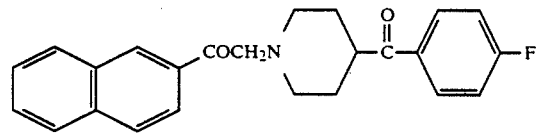

which is 2-[4-(p-fluorobenzoyl)-1-piperidinyl]-2'-acetonaphthone.

30. A cyclic amine derivative or a pharmaceutically acceptable salt of a compound of the formula:

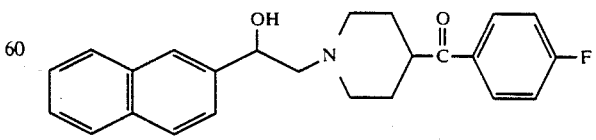

which is 2-[4-(p-fluorobenzoyl)-1-piperidinyl]-1-naphthylethanol.

31. A medicine for relieving mental symptoms due to cerebral vascular disorders, which comprises as the active ingredient an effective amount for relieving mental symptoms a cyclic amine derivative of the following formula or a pharmacologically acceptable salt thereof:

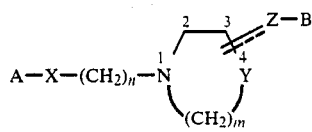

wherein A represents naphthyl optionally substituted by halogen, or lower alkyl; or the group

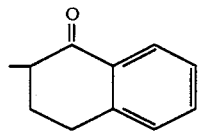

has been substituted therefor
X represents a group of the formula:

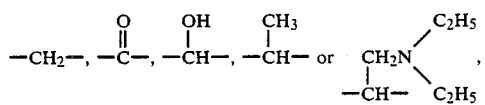

n represents an integer of 0 to 4, m represents 2, Y represents a carbon atom, Z represents a group of the formula: —$CH_2$—,

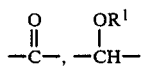

in which $R^1$ is a hydrogen atom or a lower alkyl, acyl, arylalkyl or heteroarylalkyl group,

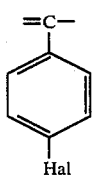

in which Hal is a halogen atom,

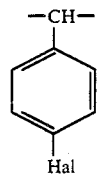

in which Hal is a halogen atom, or

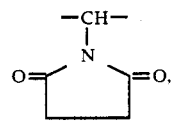

the symbol "=======" between Y and Z represents a single or double bond, the group of the formula "======= Z–B" is bonded with the ring in the above formula at the 3- or 4-position, and B represents a phenyl or naphthyl group which may be substituted with one or two substituents which may be the same or different and which are selected from the group consisting of halogens, lower alkyl groups and lower alkoxy groups; and a pharmacologically acceptable substance selected among pH adjustors, buffers, suspending agents, solubilizers, stabilizers, isotonizers and preservatives.

32. The medicine of claim 31, wherein said active ingredient is one of the following:

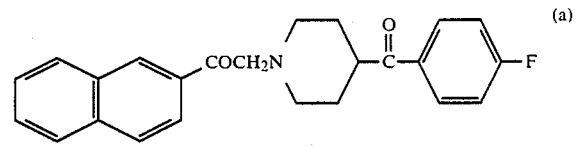

which is 2-[4-(p-fluorobenzoyl)piperidinyl]-2'-acetonaphthone;

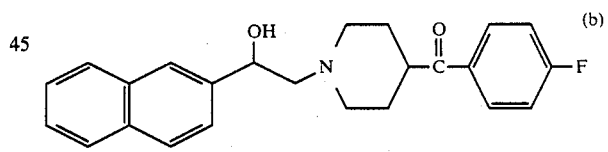

which is 2-[4-(p-fluorobenzoyl)-1-piperidinyl]-1-naphthylethanol.

* * * * *